United States Patent [19]

Etter et al.

[11] Patent Number: 4,874,672

[45] Date of Patent: * Oct. 17, 1989

[54] PLASTIC SUBSTRATE HAVING AN ADHERENT PHOTO-PRODUCT COATING ON ITS SURFACE AND A METHOD OF COATING SAID PLASTIC SUBSTRATE

[75] Inventors: Robert M. Etter; Phillip J. Neumiller, both of Racine, Wis.

[73] Assignee: S. C. Johnson & Son, Inc., Racine, Wis.

[*] Notice: The portion of the term of this patent subsequent to Dec. 27, 2005 has been disclaimed.

[21] Appl. No.: 157,192

[22] Filed: Feb. 18, 1988

Related U.S. Application Data

[63] Continuation-in-part of Ser. No. 3,350, Jan. 14, 1987, Pat. No. 4,794,131.

[51] Int. Cl.$^4$ ............................................. B32B 27/28
[52] U.S. Cl. ..................................... 428/457; 428/458; 428/459; 428/460; 428/461; 428/462; 428/463; 428/688; 427/53.1; 427/54.1
[58] Field of Search ............... 428/457, 688, 458, 459, 428/460, 461, 462, 463; 427/53.1, 54.1; 522/173, 178; 528/126, 128; 204/157.75

[56] References Cited

U.S. PATENT DOCUMENTS

| | | | |
|---|---|---|---|
| 1,962,132 | 6/1934 | Bradshaw | 106/173.1 |
| 2,639,290 | 5/1953 | Mahler | 556/110 |
| 2,686,812 | 8/1984 | Wynn et al. | 568/322 |
| 2,693,492 | 11/1954 | Hoch | 568/322 |
| 2,773,778 | 12/1956 | Hoch et al. | 252/589 |
| 2,876,210 | 3/1959 | Wynn et al. | 524/337 |
| 2,989,416 | 6/1961 | Standish | 428/263 |
| 3,043,709 | 7/1962 | Amborski | 428/216 |
| 3,049,443 | 8/1962 | Coleman | 8/527 |
| 3,098,863 | 7/1963 | Dessauer et al. | 556/150 |
| 3,100,716 | 8/1963 | Kibler et al. | 106/187 |
| 3,206,428 | 9/1965 | Stanley | 524/241 |
| 3,216,969 | 11/1965 | Cyba | 524/204 |
| 3,296,191 | 1/1967 | Smallwood | 524/328 |
| 3,361,709 | 1/1968 | Brown | 524/328 |
| 3,413,263 | 11/1968 | Strobel | 524/328 |
| 3,448,133 | 6/1969 | Strobel | 556/150 |
| 3,460,960 | 8/1969 | Francel et al. | 428/336 |
| 3,464,953 | 9/1969 | Newland | 524/202 |
| 3,616,367 | 10/1971 | Zunker | 522/21 |
| 3,642,690 | 2/1972 | Mills | 524/100 |
| 3,755,450 | 8/1973 | Anderson | 568/304 |
| 3,772,354 | 11/1978 | Fredricks | 556/45 |
| 3,786,021 | 1/1974 | Mathis | 524/204 |
| 3,871,901 | 3/1975 | Carlsson | 366/222 |
| 3,997,464 | 12/1976 | Tucker | 252/588 |
| 3,998,752 | 12/1976 | Haacke | 252/587 |
| 4,029,684 | 6/1977 | Avar et al. | 556/150 |
| 4,097,454 | 6/1978 | Tozzi et al. | 524/302 |
| 4,228,066 | 10/1980 | Johnson | 524/162 |

OTHER PUBLICATIONS

BASF Wyandotte Corporation Technical Data, "UNIMAL UV Absorbers, for Cosmetics, Plastics, Coatings, Textiles".

A Substrate Having an Adherent Photo-Product Coating on its Surface and a Method of Coating Said Substrate (Commonly Assigned Co-Pending patent application) (Ser. No. 049,062, filed May 12, 1987).

*Primary Examiner*—Lewis T. Jacobs
*Assistant Examiner*—David Buttner

[57] ABSTRACT

This invention relates to a plastic substrate having on its surface an adherent photo-product coating, and a method for coating that substrate, which coating is formed by exposing to light in the presence of an oxygen source, a reactant mixture comprising: 2,2'4,4'-tetrahydroxybenzophenone, with (1) ammonium hydroxide and optionally a trace amount of at least one reactive metal, or (2) ammonium hydroxide and at least one metal salt, or (3) at least one metal salt and at least one amine, or (4) ammonium hydroxide, at least one metal salt and at least one amine; in a suitable solvent.

17 Claims, 3 Drawing Sheets

PLASTIC SUBSTRATE HAVING AN ADHERENT PHOTO-PRODUCT COATING ON ITS SURFACE AND A METHOD OF COATING SAID PLASTIC SUBSTRATE

This application is a continuation-in part of-commonly assigned, co-pending application, Ser. No. 003,350, filed 1-19-87, now U.S. Pat. No. 4,794,414 entitled "A Photo-Product Energy Barrier Composition".

The present invention relates to a substrate having an adherent photo-product coating, and a method for coating a substrate with that photo-product composition. More particularly, it relates to a photo-product coating adhered to the surface of a plastic substrate, and a method for producing such a structure by coating a plastic substrate with a substituted benzophenone reactant mixture which is exposed to light in the presence of an oxygen source.

Benzophenones and substituted benzophenones are well known as ultraviolet light absorbers. See for example, BASF Wyandotte Corporation's Technical Data entitled "UVIMUL UV Absorbers, For Cosmetics, Plastics, Coatings, Textiles", which discloses numerous substituted benzophenones, and 2,2',4,4'-tetrahydroxybenzophenone in particular, as useful absorbers of ultraviolet light for a variety of applications. Additionally, Smallwood et al., U.S. Pat. No. 3,296,191, discloses that thermally-produced nickel or cobalt derivatives of specified hydroxybenzophenones, which do not include 2,2',4,4'-tetrahydroxybenzophenone, are useful as light and heat stabilizers for polypropylenes. The disclosed benzophenones are 2,2'-dihydroxy-4-alkoxybenzophenones with $C_6$-$C_{20}$ alkyl radicals being required for effective stabilization. Additionally, the coordination complex contains no more than about one mole of metal for every two moles of benzophenone.

U.S. Pat. No. 2,989,416 to Standish, however, states that these materials, in general, are not entirely satisfactory because of the difficulty in applying them to surfaces and the relative ease by which they are washed from such surfaces. Standish addresses such problems by reacting certain ortho-hydroxyl substituted benzophenones, with a trivalent metal, either chromium or aluminum, in molar ratios of benzophenone to metal ranging from 1:0.5 to 1:10 to form water-soluble Werner complexes that absorb longer wavelength ultraviolet radiation. The Standish product is a thermally produced compound, not a composition produced by a photo reaction.

More specifically, it is an object of this invention to provide a plastic substrate having on its surface an adherent photo-product coating. The coating provides an effective screen against ultraviolet and infrared radiation.

Still more specifically, it is an object of this invention to provide a photo-product coating that strongly adheres to plastic substrates including polyethylene, polypropylene, polyvinylchloride, polystyrene, the copolymerization product of styrene and acrylonitrile. styrene and butadiene, a phenol formaldehyde condensation product, an epoxy resin, an elastomer, a polysulfone, a polycarbonate, a polyamide, a polyacetal, a polyphenylene oxide, a urea formaldehyde condensation product, a melamine formaldehyde condensation product, a polyester resin, acrylic acid ester polymers, polyvinylacetate and polytetrafluoroethylene.

These and additional objectives are shown from the description below.

SUMMARY OF THE INVENTION

In the substrate embodiment, this invention consists of a plastic substrate having on its surface an adherent photo-product coating, which coating is formed by exposing to light in the presence of an oxygen source, a reactant mixture ("Reactant Mixture I") comprising (a) 2,2',4,4'-tetrahydroxybenzophenone, (b) ammonium hydroxide, and (c) optionally a trace amount of at least one reactive metal, in a solvent.

In a further substrate embodiment, the reactant mixture ("Reactant Mixture II") comprises (a) 2,2',4,4'-tetrahydroxybenzophenone, (b) ammonium hydroxide, and (c) at least one metal salt, in a solvent.

In still another substrate embodiment, the reactant mixture ("Reactant Mixture III") comprises (a) 2,2',4,4'-tetrahydroxybenzophenone, (b) at least one metal salt, and (c) at least one amine, in a solvent.

In still a further substrate embodiment, the reactant mixture ("Reactant Mixture IV") comprises (a) 2,2',4,4'-tetrahydroxybenzophenone, (b) ammonium hydroxide, (c) at least one metal salt, and (d) at least one amine, in a solvent.

In the method embodiment, this invention consists of a method of forming an adherent photo-product coating on the surface of a plastic substrate comprising the steps of (1) preparing a reactant mixture comprising (a) 2,2',4,4'-tetrahydroxybenzophenone, (b) ammonium hydroxide, and (c) optionally a trace amount of at least one reactive metal, in a solvent; (2) contacting said substrate with said reactant mixture; and (3) exposing said reactant mixture in contact with said substrate to light in the presence of an oxygen source. ("Method of Reactant Mixture I").

In another method embodiment, the reactant mixture comprises (a) 2,2',4,4'-tetrahydroxybenzophenone, (b) ammonium hydroxide, and (c) at least one metal salt, in a solvent. ("Method of Reactant Mixture II").

In still another method embodiment, the reactant mixture comprises (a) 2,2',4,4'-tetrahydroxybenzophenone, (b) at least one metal salt, and (c) at least one amine, in a solvent. ("Method of Reactant Mixture III").

In still a further method embodiment, the reactant mixture comprises (a) 2,2',4,4'-tetrahydroxybenzophenone, (b) ammonium hydroxide, (c) at least one metal salt, and (d) at least one amine, in a solvent. ("Method of Reactant Mixture IV").

It has been surprisingly found that 2,2',4,4'-tetrahydroxybenzophenone (THBP) in combination with (1) ammonium hydroxide, or (2) ammonium hydroxide and at least one metal salt, or (3) at least one metal salt and at least one amine, or (4) ammonium hydroxide, at least one metal salt and at least one amine; in a suitable solvent, produces an adherent photo-product coating on the surface of a plastic substrate upon exposure to light in the presence of oxygen.

It has been additionally found that the photo-product coatings of this invention tenaciously adhere to many plastic substrates including polyethylene, polypropylene, polyvinylchloride, polystyrene, the copolymerization product of styrene and acrylonitrile, styrene and butadiene, a phenol formaldehyde condensation product, an epoxy resin, an elastomer, a polysulfone, a polycarbonate, a polyamide, a polyacetal, a polyphenylene oxide, a urea formaldehyde condensation product, a melamine-formaldehyde condensation product, a polyester resin, acrylic acid ester polymers, polyvinylacetate and polytetrafluoroethylene, and are insoluble in water and many organic solvents and therefore resist removal from these substrates once applied.

DETAILED DESCRIPTION OF THE INVENTION

In one embodiment, the invention consists of a plastic substrate having on its surface an adherent photo-product coating, which coating is formed by exposing to light in the presence of an oxygen source, a reactant mixture ("Reactant Mixture I") comprising (a) 2,2',4,4'-tetrahydroxybenzophenone; (b) ammonium hydroxide; and (c) optionally a trace amount of at least one reactive metal; in a solvent.

Additionally, the method of forming an adherent photo-product coating on the surface of a plastic substrate comprising the steps of (1) preparing Reactant Mixture I in a solvent; (2) contacting said substrate with said reactant mixture; and (3) exposing said reactant mixture in contact with said substrate to light in the presence of an oxygen source; is within the scope of this invention.

In this and other more preferred embodiments of this invention, the benzophenone found best to meet the objectives of this invention and provide a photo-product coating is 2,2',4,4'-tetrahydroxybenzophenone. Other benzophenones that do not yield the present photo-product coating include 2,2'-dihydroxybenzophenone; 2,2'-dihydroxy 4,4'-dimethoxybenzophenone; 4,4'-dihydroxybenzophenone; and 2,4'-dihydroxybenzophenone. These particular benzophenones were tested by the Method of Reactant Mixture IV and found to give various precipitants without producing a photo-product coating of this invention.

Additionally, certain sources of ammonium ion ($NH_4+$) and hydroxyl ion (—OH) other than ammonium hydroxide have not proven effective in producing the photo-product coating of this invention. For example, benzyltrimethyl ammonium hydroxide, tetramethyl ammonium hydroxide, ammonium bromide and ammonium acetate, all failed to produce the requisite photo-product coating when utilized as substitutes for ammonium hydroxide in the Method of Reactant Mixture IV.

The reactive metal can be employed in elemental form or as an organic or inorganic compound, providing that it is capable of reacting with the solvated, ammoniated THBP. It is postulated that the reactive metal in its cationic form promotes formation of a stable photo-product. In certain cases, elemental metal, such as nickel, can be employed in powder form or the like. Such forms are adapted to be readily solubilized as an hydroxide or oxide. For most purposes, however, metal organoates or metal inorganic salts are preferred.

In the Method of Reactant Mixture I, a reactive metal need not be added to the mixture of reactants. X-ray analysis, however, has shown that when combining THBP and ammonium hydroxide in the presence of a solvent, trace amounts of reactive metals, in particular, zinc, are typically present as contaminants.

It is believed that the trace amounts of reactive metal assist in forming and stabilizing the photo-product. In the other reactant mixtures (mixtures II, III and IV), at least one metal salt is intentionally added to the mixture of reactants. Useful reactive metals, especially metal salts, are provided hereafter in connection with the discussion of Reactant Mixture II.

The concentration of THBP and ammonium hydroxide utilized in accordance with this aspect of the invention varies from a molar ratio of 1:1 to about 20:1, with a molar ratio of 18 moles of THBP to about 5 moles of ammonium hydroxide being preferred.

The reaction is typically carried out at room temperature (approximately 22° C.). The reaction temperature is not critical, and the addition of heat is not necessary, nor is it a limiting factor in the photo-product reaction. However, with some reactant mixtures a heat treatment may be necessary to promote the solubilization of the reactants.

The photo reaction is carried out in the presence of light, such as sunlight or artificially produced ultraviolet radiation in the range of about 200 to 400 nanometers, with about 340 to 360 nanometers being preferred. The more intense the light, particularly light in the 340 to 360 nanometer range, the more rapid the formation of the photo-product. Artificial light in this range, e.g., light produced by a mercury arc lamp, enhances the rate of photo-product formation and can, under certain circumstances, provide a coating visible to the naked eye in a few hours. Additionally, this photo-product coating adheres less tenaciously to various substrates as compared with those of Reactant Mixtures II and IV. The coating of Reactant Mixture I is also dissolved by dimethyl formamide.

A visible photo-product coating of Reactant Mixture I forms slowly on a polymeric substrate. While the photo-product can be detected almost instantly upon mixing the reactants under the proper conditions, it usually takes between about 2 and 3 days of exposure of Reactant Mixture I to direct sunlight before a film becomes noticeable to the naked eye.

According to this invention, photo-product coatings can be made by effecting contact of the substrate and the reactant mixture in a solvent. It is necessary only that the reaction medium be such that each of the reactants are soluble in it. Water alone can be utilized, but does not impart sufficient solubility to yield optimum results. Other suitable solvents are alcohols, with preferred solvents including lower alkanols, such as ethanol, isopropanol, n-propanol, isobutanol, n-butanol, and the like. Aqueous alcohol solvents and various mixtures of these solvents can also be utilized.

An oxygen source within the scope of this invention is molecular oxygen. Air contains sufficient oxygen to meet the objectives of this invention. Generally, sufficient dissolved oxygen will be present if the surface of the reactant mixture is exposed to a source of gaseous oxygen. It has been observed that bubbling pure molecular oxygen through the reactant mixture speeds up the reaction rate. Other oxygen sources providing molecular oxygen may also be employed. The photo-product coating will not, however, form in the absence of oxygen. For example, Reactant Mixture IV, under a nitrogen or argon atmosphere in the absence of oxygen, did not produce a photo-product coating of the present invention.

The substrates that can be utilized in accordance with the teachings of this invention in addition to those previously mentioned include homopolymers and copolymers of ethylenically unsaturated aliphatic, alicyclic, and aromatic hydrocarbons, such as polybutylene, polyisobutylene, copolymers of ethylene and propylene as well as of ethylene, propylene, and other olefinic hydrocarbons, polybutadiene, polyisoprene of natural or synthetic origin, polymers of pentene, hexene, heptene, octene, 2-methyl propene, 4-methyl hexene-(1), bicyclo-(2,2,1)-heptene-(2), pentadiene, hexadiene, 2,3-dimethyl butadiene, vinyl cyclohexene, cyclopentadiene, methyl styrene, and other olefinic hydrocarbons, polyindene, indene-coumarone resins, acrylic acid esters and methacrylic acid esters, cellulose derivatives, such as cellulose acetate, cellulose acetate butyrate, cellulose nitrate, ethyl cellulose, hydroxy ethyl cellulose, methyl cellulose, carboxy methyl cellulose and its sodium salts, furane resins, isocyanate resins such as polyurethanes, urea-formaldehyde resins, melamine-formaldehyde resins, melamine-urea-formaldehyde condensation products, polyamides, polyamide-epoxy resins, polyester resins, resorcinol-formaldehyde resins, resorcinol furfurol resins, chlorinated rubber, polysulfides, vinyl resins such as polyvinyl acetate, copolymers of vinyl acetate and vinyl alcohol, copolymers of vinyl acetate and vinyl chloride, polyvinyl alcohol, polyvinyl butyral, polyoxymethylene, polyphenylene oxide, polycarbonates, copolymers of bisphenols and epichlorohydrin, polysulfones, polyacetals, and in fact any other film forming or moldable natural or synthetic resin.

Teflon TM (polytetrafluoroethylene) is included within the list of plastic-type materials. The invention is not, however, intended to be limited by the above listed substrate materials.

The plastic substrates may be of different shapes such as in the form of films, foils, molded articles, rods, fibers, woven textile material, or the like.

Figure 1:
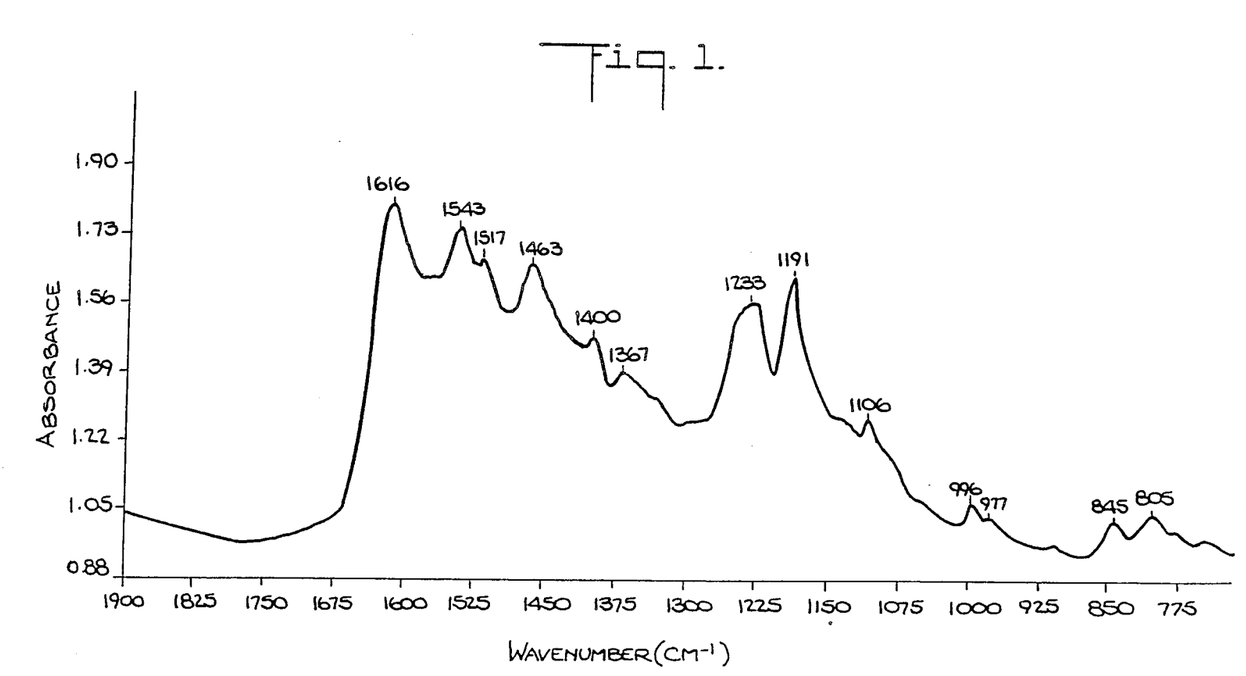
FIG. 1 is the infrared absorption spectrum for the photo-product coating of claim 8.

FIG. 1 shows the infrared absorption spectrum of one particular Reactant Mixture I photo-product coating formed by exposure to fluorescent light in the presence of air for 5 days. The reactant mixture contained 1% ammonium hydroxide, 4% THBP and 95% ethanol. Trace amounts of zinc were detected in this photo-product by x-ray analysis. The infrared absorption spectrum of FIG. 1 was determined by placing a silver chloride plate in the above mixture, and leaving the plate and reactant mixture exposed to fluorescent light in a laboratory for 5 days in a normal atmospheric environment. After 5 days, the plate was removed, washed with ethanol, then washed with acetone, dried and placed into an FTIR instrument (a Nicolet model 60SX Fourier Transform Infrared Spectrometer).

In another substrate embodiment, this invention consists of a plastic substrate having on its surface an adherent photo-product coating, which coating is formed by exposing to light in the presence of an oxygen source, a reactant mixture comprising (a) 2,2',4,4'-tetrahydroxybenzophenone; (b) ammonium hydroxide; and (c) at least one metal salt; in a solvent. Additionally, the Reactant Mixture II method of forming an adherent photo-product coating on the surface of a plastic substrate is also within the scope of this invention.

The metal salts that can be utilized in accordance with this aspect of the invention include the metal cations zinc, cadmium, copper, silver, nickel, zirconium, palladium, platinum, cobalt, rhodium, iron, ruthenium, manganese, tin, lead, polonium, mercury, and the like, and mixtures thereof, in combination with various inorganic and organic anions, such as sulfate, nitrate, bromide, chloride, acetate, formate, benzosulfonate, benzoate, and carbonate, and the like, and mixtures thereof. The preferred metal salts include nickel chloride ($NiCl_2 \cdot 6H_2O$), cobalt chloride, silver acetate, copper chloride, iron chloride, zinc acetate, lead chloride and copper acetate.

The typical concentrations of the three reactants used to form Reactant Mixture II are as follows: THBP from about 0.01% to 10%, ammonium hydroxide from about 0.01 to 10%, and metal salt from about 0.001 to 5%. All weight percents are based on the weight of the total composition.

A preferred product is formed from a ratio of at least about 18 moles of THBP, 5 moles of ammonium hydroxide, and 1 mole of a metal salt, such as nickel chloride. The maximum concentration of reactants in the process, especially THBP, is limited by solubility.

The reaction conditions described above for Reactant Mixture I apply to Reactant Mixture II, except that the photo-product reaction proceeds at a faster rate. A noticeable film is usually observed within 24 hours upon exposure to sunlight in the presence of oxygen. It is postulated that the addition of the metal salt permits the formation of an intermediate metal ligand coordination complex which improves both the energy barrier properties of the Substrate of Reactant Mixture II and the rate of reaction.

The rate of reaction is, as previously explained, dependent on the type and intensity of light. However, the rate of reactivity is, in general, also dependent on the metal cation utilized, with the general order of reactivity (from fastest to slowest) as follows: manganese, ruthenium ($Ru^{+2}$), iron ($Fe^{+2}$), rhodium ($Rh^{+2}$), cobalt ($Co^{+2}$), platinum ($Pt^{+2}$), palladium ($Pd^{+2}$), copper ($Cu^{+2}$), lead ($Pb^{+2}$), nickel ($Ni^{+2}$), cadmium ($Cd^{+2}$), and zinc ($Zn^{+2}$).

The photo-product coating of Reactant Mixture II is evidenced by the formation of a film with a polymeric appearance which forms on the substrate that is in contact with the reactants. For example, if the reactants are mixed in a glass vial, the photo-product will form and tenaciously adhere to the glass vial upon exposure to light in the presence of oxygen.

This invention, in another substrate aspect, consists of a plastic substrate having on its surface an adherent photo-product coating, which coating is formed by exposing to light in the presence of an oxygen source, a reactant mixture comprising (a) 2,2',4,4'-tetrahydroxybenzophenone; (b) at least one metal salt; and (c) at least one amine; in a solvent. Additionally, the Reactant Mixture III method of forming an adherent photo-product coating on the surface of a plastic substrate is within the scope of this invention.

The amines that are used in accordance with this invention include triethanolamine, monomethanolamine, ethanolamine, diethanolamine, butylamine, n-amylamine, and the like. In the absence of ammonium hydroxide, it is believed that the amine's sole function, in particular the preferred amine, triethanolamine, is assisting in the deprotonation of THBP prior to the photo-reaction. Regardless of the presence or absence of ammonium hydroxide, however, the amines mentioned above, including others, also have the capacity to form an amine-metal coordination complex, which is believed to complex with the deprotonated THBP during the process. Additionally, the amine-metal complex hinders the formation of insoluble metal hydroxides.

Reactant Mixture III can be conveniently utilized in commercial use. However, to inhibit the photo-reaction from occurring prior to application by the user, a stabilized formulation has been developed. In the stabilized formulation, acetic acid or carbonic acid is added to Reactant Mixture III. The pH of this formulation is typically about 6.2±0.2.

Upon application, the acetic acid volatilizes or, if carbonic acid is used, it converts to carbon dioxide and water. This raises the pH thereby allowing the THBP to be slowly deprotonated by the triethanolamine and complexed with the metal-amine. It is believed that the acetic acid or carbonic acid initially stabilizes the THBP and prevents the deprotonation reaction from occurring.

This stabilized photo-product coating initially becomes visible in about 24 hours upon exposure to sunlight in the presence of oxygen and continues reacting for on to two weeks thereafter, producing a fully-developed film within that time period.

The typical concentration ranges of the three reactants employed in Reactant Mixture III, in accordance with this invention, are as follows: about 0.01 to 10% of THBP, about 0.001 to 5% of at least one metal salt, preferably copper acetate, and about 0.01 to 2% of at least one amine, preferably triethanolamine. The amount of acetic acid or carbonic acid required to prevent deprotonization of THBP is usually the amount required to lower the pH of the reactant mixture to about 6 or below. Examples of these formulations are given in Table 2 hereafter.

Figure 2:
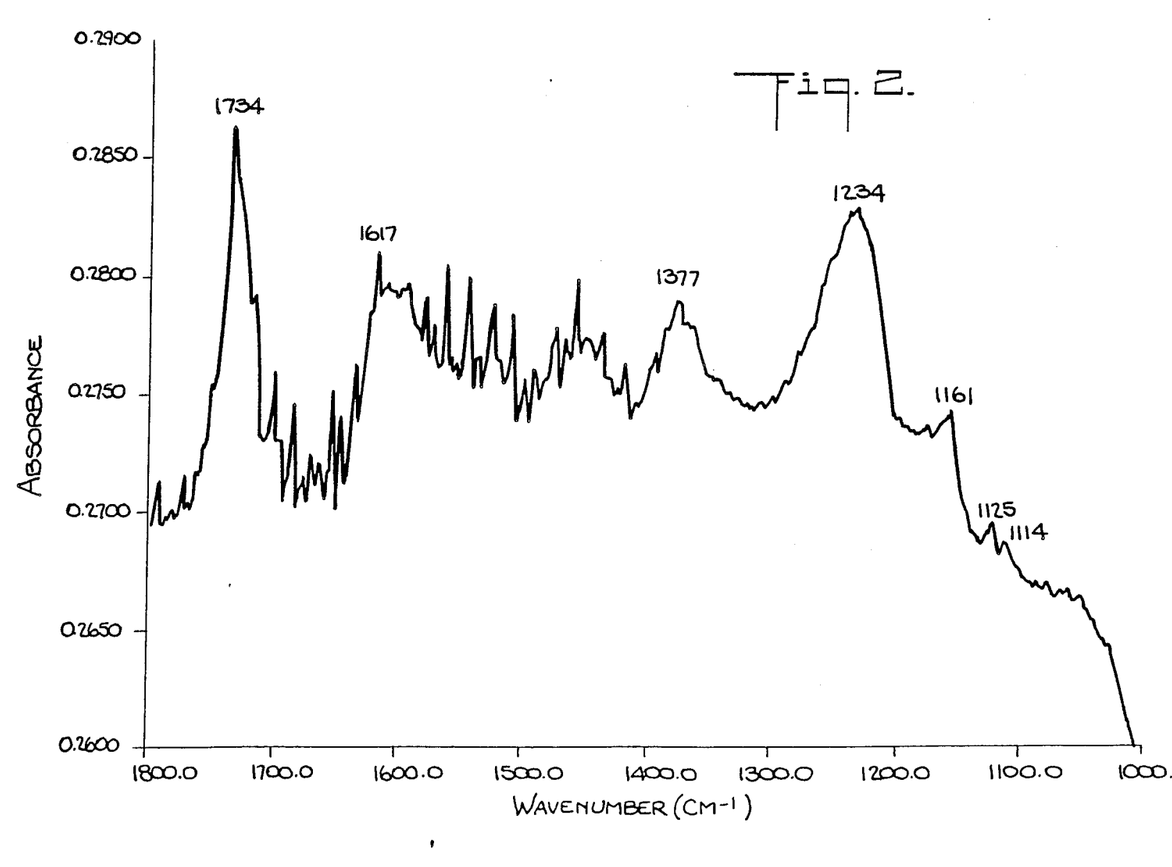
FIG. 2 is the infrared absorption spectrum for the photo-product coating of claim 9.

FIG. 2 shows the infrared absorption spectrum of one particular Reactant Mixture III photo-product coating after exposure to a mercury arc vapor lamp in the presence of air for approximately 9 hours. The reactant mixture contains 4.00% THBP, 76.75% ethanol, 4.00% deionized water, 8.00% alcohol, 1.00% triethanolamine, 0.5% acetic acid (99.9% concentration), 0.75% copper acetate, and 5.00% of a polymer consisting of 60% ethyl acrylate and 40% methylmethacrylate. The infrared absorption spectrum of FIG. 2 was determined by placing a silver chloride plate in the above mixture, and leaving the plate and reactant mixture exposed to the mercury arc vapor lamp for approximately 9 hours in a normal atmosphere. After exposure, the plate was removed, washed with ethanol, then washed with acetone, dried and placed into the FTIR.

The most preferred substrate embodiment of this invention consists of a plastic substrate having on its surface an adherent photo-product coating, which coating is formed by exposing to light in the presence of an oxygen source, a reactant mixture comprising (a) 2,2',4,4'-tetrahydroxybenzophenone; (b) ammonium hydroxide; (c) at least one metal salt; and (d) at least one amine; in a solvent.

Additionally, the Reactant Mixture IV method of forming an adherent photo-product coating on the surface of a plastic substrate is within the scope of this invention.

The only benzophenone found that meets the objectives of this invention and provides a suitable photo-product coating is 2,2',4,4'-tetrahydroxybenzophenone. Additionally, sources of ammonium and hydroxyl ion, other than ammonium hydroxide, have not proven effective in producing a photo-product coating of this invention in Reactant Mixture IV.

The formulas of the reaction products of this invention are unknown. It is postulated that, in the first step of the process, the ammonium hydroxide deprotonates the hydroxyl group adjacent to the THBP carbonyl group. Under the influence of light and oxygen, the deprotonated THBP is thought to form a diradical and then form both a coordination complex with the metal cation and an addition product with another THBP molecule.

Typical concentrations of the reactants of Reactant Mixture IV are given in Table 1 below:

TABLE 1

| | Reactant Mixture IV Formulations | | |
|---|---|---|---|
| Ingredients | General | Concentration Preferred | Most Preferred |
| THBP | 0.01 to 10% | 3.0 to 5.0% | 4.0% |
| NH$_4$OH | | | |
| (28.5% conc.) | 0.1 to 10% | 0.25 to 1.75% | 1.0% |
| (100% conc.) | 0.1 to 1% | 0.1 to 0.5% | 0.3% |
| Metal salt | 0.001 to 5% | 0.05 to 0.5% | 0.2% |
| Amine | 0.001 to 2% | 0.25 to 1% | 0.6% |
| H$_2$O | 0 to 15% | 6 to 10% | 8.0% |
| Alcohol | balance to 100% | balance to 100% | balance to 100% |

These concentrations, as well as those given above for the other reactant mixtures, are provided to illustrate the present invention, but are not to be construed as limiting the invention in terms of concentration or proportion of ingredients. Concentrations outside of these general ranges can be utilized to practice this invention.

The Method of Reactant Mixture IV is typically carried out as described above for the Methods of Reactant Mixture I and II. When the reactant mixture is contacted with a polymeric substrate and exposed to sunlight in the presence of oxygen, a visible photo-product coating is produced in a few hours, especially with the faster reacting metals, such as copper, manganese and iron. Exposure of this formulation to a mercury arc lamp in the presence of oxygen produces a visible photo-film within a few minutes.

Although applicants do not wish to be bound by any particular theory, the photo-ligand-metal-coordination complex of Reactant Mixture IV is believed to proceed as follows: THBP, preferably at least about 6 moles and more preferably at least about 18 moles, is mixed with at least 5 moles of ammonium hydroxide, in a suitable solvent, preferably an aqueous alcohol solvent, to form deprotonated THBP. The metal salt, preferably about 1 mole of a nickel salt is then mixed with 5 moles of an amine, preferably triethanolamine, to form a nickel salt-triethanolamine coordination complex. This complex is then mixed with the deprotonated THBP to form a metal-coordination complex that upon exposure to light in the presence of oxygen forms a photo-product of the present invention.

The photo-product coatings of this invention are insoluble in the reaction media and many other solvents, and therefore, are long lasting and durable. Once applied, the photo-product coatings cannot be removed without chemical treatment. To date, only strong solvents, such as dimethyl sulfoxide, appear to solubilize or form a complex with the photo-product coating to effect its removal. Additionally, dimethyl formamide will dissolve the coatings of Reactant Mixture I. It is known, however, that the photo-product coating will form water soluble salts with appropriate bases. For example, the photo film can be dissolved by any strong basic material, such as sodium, potassium or ammonium hydroxide, or mixtures thereof, at pH above 10. Typically, the film is solubilized at a pH from 10.2 to 10.5. The photo-product can be precipitated as a solid from these basic solutions by the addition of an acid, such as acetic acid, to lower the pH to below about 7.0. The pH ranges of Reactant Mixtures I, II and IV typically range from about 8.5 to 9.9.

Iodine may be used in the reactant mixtures of this invention. The iodine is mixed with the reactants prior to exposure to light. The concentration of iodine that may be utilized varies from about 0.001% to about 5%, with a range of 0.01% to 1% being preferred. These percentages are weight percents based on the total weight of the composition.

The reactant mixtures of this invention also preferably employ various polymers, such as ethyl acrylate and/or methylmethacrylate, or other alcohol-soluble resin polymers, that act as a matrix so that the reactants can be easily applied to substrates, and thereby allow the formation of the photo-product on the substrate.

Figure 3:
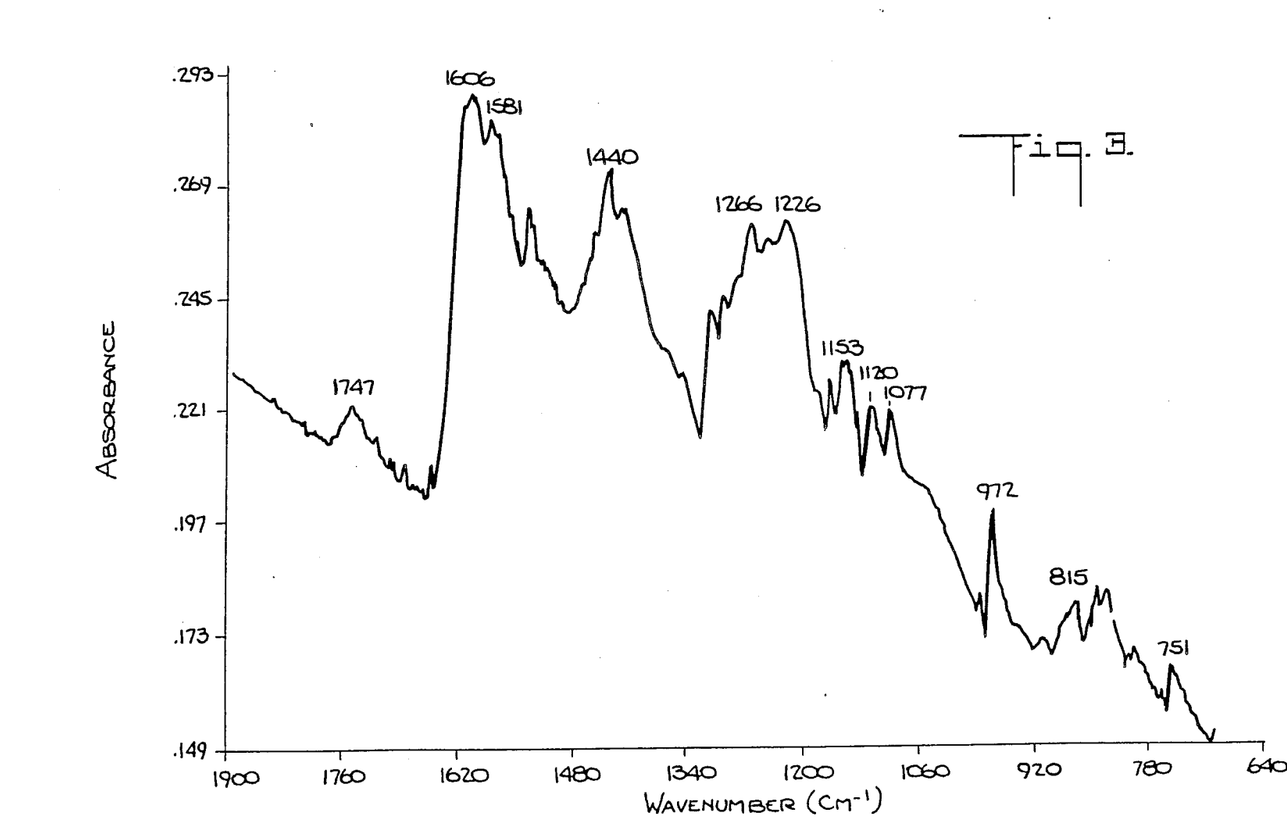
FIG. 3 is the infrared absorption spectrum for the photo-product coating of claim 10.

FIG. 3 shows the infrared absorption spectrum of one particular Reactant Mixture IV photo-product coating wherein the reactant mixture contained 4.14% THBP, 86.0% ethanol, 0.63% triethanolamine, 8.00% deionized water, 1.03% ammonium hydroxide (at 28.5% conc.) and 0.2% nickel chloride, and was exposed to fluorescent light in the presence of oxygen for four days. The absorption spectrum was determined in the same manner as described for FIGS. 1 and 2.

Other aspects and embodiments of this invention are shown in the following Examples which are illustrative of scope.

EXAMPLES 1-15

Examples 11-15 of Table 2 show typical reactant mixtures that can provide photo-product coatings in accordance with the teachings of this invention.

TABLE 2

| | Reactant Mixture III Formulations | | | | | | | | | | | | | | |
|---|---|---|---|---|---|---|---|---|---|---|---|---|---|---|---|
| | EXAMPLES | | | | | | | | | | | | | | |
| | 1 | 2 | 3 | 4 | 5 | 6 | 7 | 8 | 9 | 10 | 11 | 12 | 13 | 14 | 15 |
| Ethanol | 86.7 | 87.3 | 77.2 | 86.3 | 86.1 | 86.39 | 85.6 | 85.0 | 84.96 | 84.5 | 80.5 | 80.5 | 78.5 | 81.75 | 76.9 |
| Deionized Water | 8.0 | 8.0 | 8.0 | 8.0 | 8.0 | 8.2 | 8.1 | 8.0 | 7.99 | 8.0 | 8.0 | — | — | — | 4.0 |
| THBP | 4.0 | 4.0 | 4.0 | 4.0 | 4.0 | 3.94 | 4.0 | 4.5 | 4.59 | 4.5 | 4.0 | 2.0 | 3.5 | 4.0 | 4.0 |
| TEA | 0.5 | 0.6 | 0.6 | 1.0 | 1.0 | 1.1 | 1.07 | 1.0 | 1.1 | 1.0 | 1.0 | 1.0 | 1.0 | 1.0 | 1.0 |
| Metal Salt | $0.4^{(1)}$ | $0.2^{(2)}$ | $0.2^{(2)}$ | $0.2^{(3)}$ | $0.2^{(3)}$ | $0.5^{(3)}$ | $1.0^{(3)}$ | $1.0^{(3)}$ | $0.99^{(4)}$ | $1.0^{(3)}$ | $1.0^{(3)}$ | $1.0^{(3)}$ | $1.5^{(3)}$ | $0.75^{(3)}$ | $1.0^{(3)}$ |
| Acetic Acid (a) | 0.4 | 0.1 | 10.0 | 0.5 | 0.5 | 0.54 | 0.54 | 0.5 | 0.65 | 0.5 | 0.5 | 0.5 | 0.5 | 0.5 | $1.0^{(g)}$ |
| Stearyl (d) or benzyl (e) alcohol | — | — | — | — | $0.2^{(d)}$ | — | — | — | — | — | — | $8.0^{(e)}$ | $10.0^{(e)}$ | $10.0^{(e)}$ | $8.0^{(e)}$ | 8.0 |
| Matrix Polymer | — | — | — | — | — | — | — | — | — | — | $0.5^{(b)}$ | $5.0^{(c)}$ | $5.0^{(c)}$ | $5.0^{(c)}$ | $4.0^{(c)}$ | $5.0^{(c)}$ |

(1) silver acetate
(2) $FeCl_2 \cdot 4H_2O$
(3) copper acetate
(4) zinc acetate
(a) 99.9% concentrated acetic acid
(b) Carbsoset 525 B.F. Goodrich
(c) 60% ethyl acrylate and 40% methylmethacrylate
(g) $CO_2$ gas

EXAMPLES 16-25

The Reactant Mixture IV formulas of Table 3 also show typical reactant mixtures in accordance with the teachings of this invention.

TABLE 3

| | Reactant Mixture IV Formulations | | | | | | | | | |
|---|---|---|---|---|---|---|---|---|---|---|
| | EXAMPLES | | | | | | | | | |
| | 16 | 17 | 18 | 19 | 20 | 21 | 22 | 23 | 24 | 25 |
| Ethanol | 86.0 | 87.4 | 90.85 | 86.0 | $86.0^{(a)}$ | 86.1 | 95.4 | 86.1 | 86.2 | 86.2 |
| THBP | 4.0 | 2.0 | 3.0 | 4.14 | 4.14 | 4.0 | 2.0 | 4.0 | 4.0 | 4.0 |
| TEA | 0.5 | 0.5 | 0.75 | 0.63 | 0.63 | 0.5 | 0.5 | 0.5 | 0.6 | 0.6 |
| NH$_4$OH (28.5%) | 1.0 | 1.0 | 5.0 | 1.03 | 1.03 | 1.0 | 1.0 | 1.0 | 1.0 | 1.0 |
| Deionized Water | 8.0 | 8.0 | — | 8.0 | 8.0 | 8.0 | — | 8.0 | 8.0 | 8.0 |
| Metal Salt | $0.5^{(1)}$ | $0.1^{(1)}$ | $0.4^{(1)}$ | $0.2^{(1)}$ | $0.2^{(1)}$ | $0.4^{(2)}$ | $0.1^{(3)}$ | $0.4^{(4)}$ | $0.2^{(5)}$ | $0.2^{(6)(7)}$ |
| Benzyl Alcohol | 1.0 | — | — | — | — | — | 1.0 | — | — | — |

(1) $NiCl_2 \cdot H_2O$
(2) silver acetate
(3) iron chloride ($FeCl_2 \cdot H_2O$)
(4) copper acetate monohydrate
(5) $MnCl_2 \cdot 4H_2O$
(6) $ZnCl_2$
(7) $CuCl_2 \cdot H_2O$
(a) isopropanol

EXAMPLE 26

In this example, an RCA Compact Digital Audio Disc made from a plastic material was placed in a reactant mixture bath and exposed to a Gates MLA medium pressure 85 watt mercury arc lamp at a distance of 3 inches from the substrate for approximately 3 hours at room temperature and normal atmospheric conditions. It was then left in the bath for an additional 17 hours prior to removal. The reactant mixture consisted of 4.0% THBP, 84.3% ethanol, 0.6% triethanolamine, 10.0% deionized water, 1.0% ammonium hydroxide (28.5% concentration) and 0.1% lead chloride. After exposure, the coated compact disc substrate was washed with ethanol and blow dried. A pink coating approximately 2000 Angstroms thick was formed.

EXAMPLES 27-32

In these examples, a number of different plastic substrates were photo-coated using the same procedure as described in Example 26. The reactant mixture in each case consisted of 4.14% THBP, 86.0% ethanol, 0.63% triethanolamine, 8.0% deionized water, 1.03% ammonium hydroxide (28.5% concentration) and 0.2% nickel chloride. The plastics utilized are shown in Table 4 below.

TABLE 4

| Example | Plastic Substrate |
| --- | --- |
| 27 | High density polyethylene |
| 28 | Polyethylene terephthalate polyester |
| 29 | Polypropylene |
| 30 | Polystyrene |
| 31 | Polyvinyl chloride |
| 32 | Polyacrylonitrilemethylacrylate. (Barex 210) |

Each of these plastics were five centimeters square by one millimeter thick. All surfaces were generally smooth except for polyethylene, which was similar to a matted finish.

Each was placed in the above reactant mixture and exposed to the mercury arc lamp for approximately 3 hours at room temperature and normal atmospheric conditions. After an additional 17 hours in the reactant mixture bath the samples were removed and washed with alcohol. All plastics were coated with a blue green nickel film.

EXAMPLES 33-38

The same plastics utilized in examples 27-32 were exposed to a reactant mixture bath which consisted of 4.0% THBP, 84.3% ethanol, 0.6% triethanolamine, 10.0% deionized water, 1.0% ammonium hydroxide (28.5% concentration) and 0.1% lead chloride. The same conditions discussed in examples 27-32 were utilized with these examples. A pink coating was present on all substrates.

EXAMPLES 39-41

In these examples, strips of Virgin Teflon TM (TFE Sht 860227) were contacted with three different reactant mixtures. In Example 39, the reactant mixture consisted of 4.14% THBP, 86.0% ethanol, 0.63% triethanolamine, 8.0% deionized water, 1.03% ammonium hydroxide (28.5% concentration) and 0.2% nickel chloride. In Example 40, the reactant mixture consisted of 4.0% THBP, 85.2% ethanol, 0.6% triethanolamine, 8.0% deionized water, 1.0% ammonium hydroxide (28.5% concentration), 0.2% copper acetate and 1.0% iodine. In Example 41, the reactant mixture consisted of 4.0% THBP, 8.0% deionized water, 1.0% ammonium hydroxide (28.5% concentration) and 0.2% lead chloride.

The Teflon TM samples were placed in these formulas and exposed to sunlight in a laboratory window for approximately 48 hours (about 24 hours of which constituted daylight) at room temperature and normal atmospheric conditions.

All three reactant mixtures produced a heavy photocoating on the Teflon TM surface and while excess amounts of each coating or film was abraded from the surface, it was not possible to abrade all the coating from the surface.

EXAMPLES 42-48

Additional examples of reactant mixtures within the teachings of the invention are:

Example 42: 4.0% 2,2',4,4'-tetrahydroxybenzophenone, 86.2% ethanol, 0.6% triethanolamine, 8.0% deionized water, 1.0% ammonium hydroxide (28.5% conc.), and 0.2% $HgCl_2$.

Example 43: 4.0% 2,2',4,4'-tetrahydroxybenzophenone, 86.2% ethanol, 0.6% triethanolamine, 8.0% deionized water, 1.0% ammonium hydroxide (28.5% conc.), and 0.2% $PdCl_2$.

Example 44: 4.0% 2,2',4,4'-tetrahydroxybenzophenone, 86.2% ethanol, 0.6% triethanolamine, 8.0% deionized water, 1.0% ammonium hydroxide (28.5% conc.), and 0.2% $CdCl_2$.

Example 45: 4.0% 2,2',4,4'-tetrahydroxybenzophenone, 86.2% ethanol, 0.6% triethanolamine, 8.0% deionized water, 1.0% ammonium hydroxide (28.5% conc.), and 0.2% $RuCl_3$.

Example 46: 4.0% 2,2',4,4'-tetrahydroxybenzophenone, 86.2% ethanol, 0.6% triethanolamine, 8.0% deionized water, 1.0% ammonium hydroxide (28.5% conc.), and 0.2% $ZrO_2$.

Example 47: 4.0% 2,2',4,4'-tetrahydroxybenzophenone, 86.2% ethanol, 0.6% triethanolamine, 8.0% deionized water, 1.0% ammonium hydroxide (28.5% conc.), and 0.2% $RhCl_3$.

Example 48: 3.0% 2,2',4,4'-tetrahydroxybenzophenone, 2.0% triethanolamine, 0.1% cobalt chloride ($CoCl_2$), and 94.9% ethanol.

What is claimed is:

1. A plastic substrate having on its surface an adherent photo-product coating, which coating is formed by exposing to light in the presence of an oxygen source, a reactant mixture having a pH from about 7 to 10.5 comprising:
    (a) 2,2',4,4'-tetrahydroxybenzophenone;
    (b) ammonium hydroxide; and
    (c) optionally a trace amount of at least one reactive metal selected from the group consisting of zinc, copper, nickel, silver, iron, manganese, lead, cobalt, zirconium, mercury, palladium, cadmium, ruthenium, rhodium, and mixtures thereof;
in a solvent.

2. A plastic substrate having on its surface an adherent photo-product coating, which coating is formed by exposing to light in the presence of an oxygen source, a reactant mixture having a pH from about 7 to 10.5 comprising:
    (a) 2,2',4,4'-tetrahydroxybenzophenone;
    (b) ammonium hydroxide; and
    (c) at least one metal salt wherein the metal is selected from the group consisting of zinc, copper, nickel, silver, iron, manganese, lead, cobalt, zirconium, mercury, palladium, cadmium, ruthenium, rhodium, and mixtures thereof;
in a solvent.

3. A plastic substrate having on its surface an adherent photo-product coating, which coating is formed by exposing to light in the presence of an oxygen source, a reactant mixture having a pH from about 7 to 10.5 comprising:
   (a) 2,2,',4,4'-tetrahydroxybenzophenone:
   (b) at least one metal salt wherein the metal selected from the group consisting of zinc, copper, nickel, silver, iron, manganese, lead, cobalt, zirconium, mercury, palladium, cadmium, ruthenium, ohodium, and mixtures thereof; and
   (c) at least one amine;
in a solvent.

4. A plastic substrate having on its surface an adherent photo-product coating, which coating is formed by exposing to light in the presence of an oxygen source, a reactant mixture having a pH from about 7 to 10.5 comprising:
   (a) 2,2',4,4'-tetrahydroxybenzophenone;
   (b) ammonium hydroxide;
   (c) at least one metal salt wherein the metal is selected from the group consisting of zinc, copper, nickel, silver, iron, manganese, lead, cobalt, zirconium, mercury, palladium, cadmium, ruthenium, rhodium, and mixtures thereof; and
   (d) at least one amine;
in a solvent.

5. The substrate of claims 2, 3 or 4 wherein the metal salt is selected from the group consisting of nickel chloride, cobalt chloride, silver acetate, iron chloride, copper acetate, lead chloride, zinc acetate, copper chloride and mixtures thereof.

6. The substrate of claims 3 or 4 wherein the amine is selected from the group consisting of triethanolamine, diethanolamine, ethanolamine, monomethanolamine, butylamine, n amylamine and mixtures thereof.

7. The substrate of claims 1, 2, 3 or 4 in which the plastic substrate is selected from the group consisting of polyethylene, polypropylene, polyvinylchloride, polystyrene, the copolymerization product of styrene and acrylonitrile, styrene and butadiene, a phenolformaldehyde condensation product, an epoxy resin, an elastomer, a polysulfone, a polycarbonate, a polyamide, a polyacetal, a polyphenylene oxide, a urea-formaldehyde-condensation product, a melamine-formaldehyde condensation product, a polyester resin, acrylic acid ester polymers, polyvinylacetate and polytetrafluoroethylene.

8. A plastic substrate having on its surface an adherent photo-product coating containing the elements carbon, hydrogen, oxygen, nitrogen and a trace amount of zinc; exhibiting characteristic absorption peaks in the infrared region of the spectrum, when cast as a film on a silver chloride plate at the following frequencies expressed in reciprocal centimeters: 1616, 1543, 1517, 1463, 1400, 1367, 1233, 1191, 1106, 996, 977, 845 and 805; and formed by exposing to light in the presence of an oxygen source, a reactant mixture comprising: 2,2',4,4'-tetrahydroxybenzophenone, ammonium hydroxide and a trace amount of zinc.

9. A plastic substrate having on its surface an adherent photo-product coating containing the elements carbon, hydrogen, nitrogen, oxygen and copper; exhibiting characteristic absorption peaks in the infrared region of the spectrum, when cast as a film on a silver chloride plate at the following frequencies expressed in reciprocal centimeters: 1734, 1617, 1377, 1234, 1161, 1125, and 1114; and formed by exposing to light in the presence of an oxygen source, a reactant mixture comprising: 2,2',4,4'-tetrahydroxybenzophenone, triethanolamine and copper cation.

10. A plastic substrate having on its surface an adherent photo-product coating containing the elements carbon, hydrogen, nitrogen, oxygen and nickel; exhibiting characteristic absorption peaks in the infrared region of the spectrum, when cast as a film on a silver chloride plate, at the following frequencies expressed in reciprocal centimeters: 1747, 1606, 1581, 1440, 1266, 1226, 1153, 1120, 1097, 972, 875 and 751; and formed by exposing to light in the presence of an oxygen source a reactant mixture comprising: 2,2',4,4'-tetrahydroxybenzophenone, triethanolamine, ammonium hydroxide and nickel cation.

11. A method of forming an adherent photo-product coating on the surface of a plastic substrate comprising the steps of:
   (1) preparing the reactant mixture of claim 1;
   (2) contacting said substrate with said reactant mixture; and
   (3) exposing said reactant mixture in contact with said substrate to light in the presence of an oxygen source.

12. A method of forming an adherent photo-product coating on the surface of a plastic substrate comprising the steps of:
   (1) preparing a reactant mixture of claim 2;
   (2) contacting said substrate with said reactant mixture; and
   (3) exposing said reactant mixture in contact with said substrate to light in the presence of an oxygen source.

13. A method of forming an adherent photo-product coating on the surface of a plastic substrate comprising the steps
   (1) preparing a reactant mixture of claim 3;
   (2) contacting said substrate with said reactant mixture; and
   (3) exposing said reactant mixture in contact with said substrate to light in the presence of an oxygen source.

14. A method of forming an adherent photo-product coating on the surface of a plastic substrate comprising the steps of:
   (1) preparing a reactant mixture of claim 4;
   (2) contacting said substrate with said reactant mixture; and
   (3) exposing said reactant mixture in contact with said substrate to light in the presence of an oxygen source.

15. The method of claims 13 or 14 wherein the metal salt is selected from the group consisting of nickel chloride, cobalt chloride, silver acetate, iron chloride, copper acetate, lead chloride, zinc acetate, copper chloride and mixtures thereof.

16. The method of claims 13 or 14 wherein the amine is selected from the group consisting of triethanolamine, diethanolamine, ethanolamine, monomethanolamine, butylamine, n-amylamine and mixtures thereof.

17. The method of claims 11, 12, 13 or 14 wherein said plastic substrate is selected from the group consisting of polyethylene, polypropylene, polyvinylchloride, polystyrene, the copolymerization product of styrene and acrylonitrile, styrene and butadiene, a phenol-formaldehyde condensation product, an epoxy resin, an elastomer, a polysulfone, a polycarbonate, a polyamide, a polyacetal, a polyphenylene oxide, a urea-formaldehyde-condensation product, a melamine-formaldehyde condensation product, a polyester resin, acrylic acid ester polymers, polyvinylacetate and polytetrafluoroethylene.

* * * * *

UNITED STATES PATENT AND TRADEMARK OFFICE
CERTIFICATE OF CORRECTION

PATENT NO. : 4,874,672

DATED : October 17, 1989

INVENTOR(S) : Etter et al.

It is certified that error appears in the above-identified patent and that said Letters Patent is hereby corrected as shown below:

At column 13, line 39, please substitute "n amylamine" with -- n-amylamine --.

At column 14, line 39, following the word steps, please add -- of: --.

Signed and Sealed this

Second Day of July, 1991

Attest:

Attesting Officer

HARRY F. MANBECK, JR.

Commissioner of Patents and Trademarks